US012778502B2

(12) United States Patent
Pi et al.

(10) Patent No.: US 12,778,502 B2
(45) Date of Patent: Nov. 3, 2026

(54) HEAT CONSUMPTION ESTIMATION METHOD AND APPARATUS, AND STORAGE MEDIUM

(71) Applicant: Beijing Xiaomi Mobile Software Co., Ltd., Beijing (CN)

(72) Inventors: Te Pi, Beijing (CN); Lifeng Yao, Beijing (CN); Guosong Gao, Beijing (CN); Sanbao Li, Beijing (CN)

(73) Assignee: BEIJING XIAOMI MOBILE SOFTWARE CO., LTD., Beijing (CN)

( * ) Notice: Subject to any disclaimer, the term of this patent is extended or adjusted under 35 U.S.C. 154(b) by 93 days.

(21) Appl. No.: 18/716,502

(22) PCT Filed: May 13, 2022

(86) PCT No.: PCT/CN2022/092874

§ 371 (c)(1),
(2) Date: Jun. 4, 2024

(87) PCT Pub. No.: WO2023/216267

PCT Pub. Date: Nov. 16, 2023

(65) Prior Publication Data

US 2025/0025100 A1 Jan. 23, 2025

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/11*** | (2006.01) |

(52) U.S. Cl.

CPC .......... *A61B 5/4866* (2013.01); *A61B 5/0205* (2013.01); *A61B 5/7278* (2013.01); *A61B 5/02438* (2013.01); *A61B 5/11* (2013.01); *A61B 2503/10* (2013.01)

(58) Field of Classification Search

CPC .............. A61B 2503/10; A61B 5/0205; A61B 5/02405; A61B 5/02438; A61B 5/11; A61B 5/1118; A61B 5/4866; A61B 5/7278; G16H 50/30

See application file for complete search history.

(56) References Cited

U.S. PATENT DOCUMENTS

| | | | |
|---|---|---|---|
| 2003/0028116 | A1 | 2/2003 | Bimbaum |
| 2015/0289790 | A1 | 10/2015 | Swenson |
| 2016/0058370 | A1 | 3/2016 | Raghuram et al. |

FOREIGN PATENT DOCUMENTS

| | | | |
|---|---|---|---|
| CN | 102727185 | A | 10/2012 |
| CN | 105574311 | A | 5/2016 |
| CN | 106264451 | A | 1/2017 |
| CN | 107438398 | A | 12/2017 |

(Continued)

*Primary Examiner* — Michael T Rozanski

(74) *Attorney, Agent, or Firm* — McCoy Russell LLP

(57) ABSTRACT

A heat consumption estimation method includes: obtaining the heart rate of a target user at a current moment; determining motion state feature information of the target user at the current moment, where the motion state feature information is configured to represent whether the target user is in a motion steady-state stage or a motion recovery stage at the current moment; and determining, according to the motion state feature information and the heart rate at the current moment, total heat consumption information of the target user in a motion process, where the motion process includes a process from a motion starting moment to the current moment.

15 Claims, 5 Drawing Sheets

(56) References Cited

FOREIGN PATENT DOCUMENTS

| | | | |
|---|---|---|---|
| CN | 110381833 | A | 10/2019 |
| CN | 110457995 | A | 11/2019 |
| CN | 112384984 | A | 2/2021 |
| TW | 201121503 | A | 7/2011 |

HEAT CONSUMPTION ESTIMATION METHOD AND APPARATUS, AND STORAGE MEDIUM

CROSS-REFERENCE TO RELATED APPLICATIONS

The present application is a U.S. National Stage of International Application No. PCT/CN2022/092874, entitled "HEAT CONSUMPTION ESTIMATION METHOD AND DEVICE AND STORAGE MEDIUM", filed on May 13, 2022, the contents of all of which are incorporated herein by reference in their entireties for all purposes.

BACKGROUND

With the continuous development of a technology, a wearable device has gradually entered people's daily life. The wearable device refers to a portable device that is directly worn on the body or integrated into the user's clothing, and has diverse product forms, such as a smartwatch, a smart bracelet, smart glasses, and a smart helmet and so on. The wearable device has many sensors that can collect physiological signals from the human body, such as a heart rate and other signals, so as to monitor health indicators of a user. In monitoring of indicators about motion, heat consumption, namely, calorie consumption, of the user in a motion process has been becoming an object of increasing concern for people.

SUMMARY

The disclosure relates to the field of human-computer interaction, in particular to a heat consumption estimation method and apparatus, and a storage medium.

According to a first aspect of an example of the disclosure, a heat consumption estimation method is provided, including:

- obtaining a heart rate of a target user at a current moment;
- determining motion state feature information of the target user at the current moment, where the motion state feature information is configured to represent whether the target user is in a motion steady-state stage or a motion recovery stage at the current moment; and
- determining, according to the motion state feature information and the heart rate at the current moment, total heat consumption information of the target user in a motion process, where the motion process includes a process from a motion starting moment to the current moment.

According to a second aspect of an example of the disclosure, a heat consumption estimation apparatus is provided, including:

- a heart rate obtaining module, configured to obtain a heart rate of a target user at a current moment;
- a state determining module, configured to determine motion state feature information of the target user at the current moment, where the motion state feature information is configured to represent whether the target user is in a motion steady-state stage or a motion recovery stage at the current moment; and
- a heat determining module, configured to determine, according to the motion state feature information and the heart rate at the current moment, total heat consumption information of the target user in a motion process, where the motion process includes a process from a motion starting moment to the current moment.

According to a third aspect of an example of the disclosure, a heat consumption estimation apparatus is provided, including:

- a processor; and
- a memory, configured to store executable instructions of the processor;
- the processor is configured to:
- obtain a heart rate of a target user at a current moment;
- determine motion state feature information of the target user at the current moment, wherein the motion state feature information is configured to represent whether the target user is in a motion steady-state stage or a motion recovery stage at the current moment; and
- determine, according to the motion state feature information and the heart rate at the current moment, total heat consumption information of the target user in a motion process, wherein the motion process comprises a process from a motion starting moment to the current moment.

According to a fourth aspect of an example of the disclosure, a non-transitory computer readable storage medium is provided, storing a computer program instruction. The computer program instruction, when being executed by a processor configures the processor to:

- obtain a heart rate of a target user at a current moment;
- determine motion state feature information of the target user at the current moment, wherein the motion state feature information is configured to represent whether the target user is in a motion steady-state stage or a motion recovery stage at the current moment; and
- determine, according to the motion state feature information and the heart rate at the current moment, total heat consumption information of the target user in a motion process, wherein the motion process comprises a process from a motion starting moment to the current moment.

It is to be understood that the above general description and the following detailed description are for example and explanatory, and cannot limit the disclosure.

BRIEF DESCRIPTION OF DRAWINGS

Accompanying drawings here, which are incorporated in and constitute a part of specification, illustrate examples consistent with the disclosure and together with the specification, serve to explain the principles of the disclosure.

DETAILED DESCRIPTION

Figure 1:
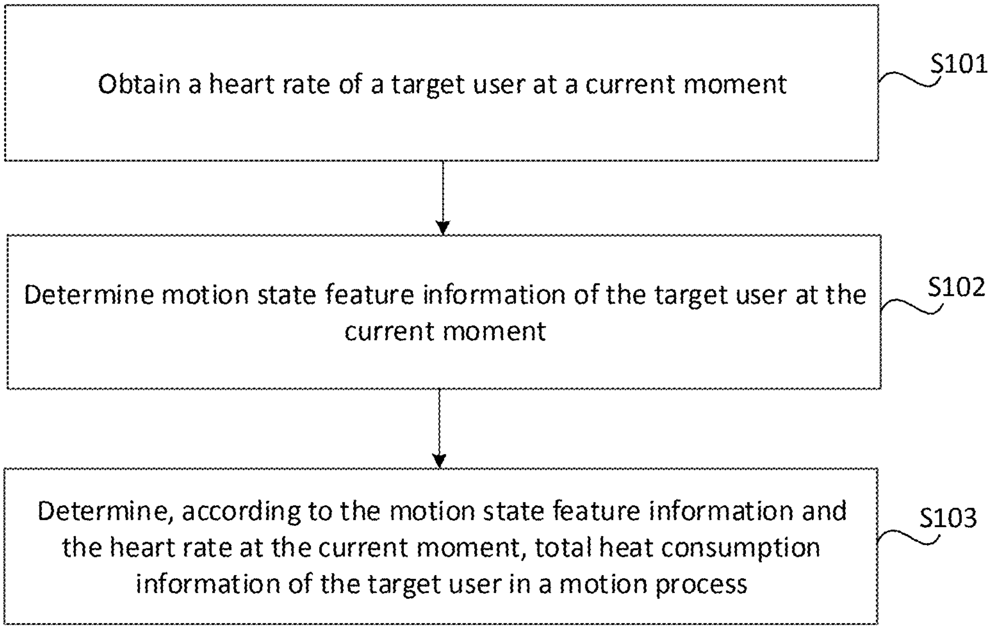
FIG. 1 is a flow diagram of a heat consumption estimation method shown according to an example.

Examples will be illustrated in detail here, and instances of which are represented in accompanying drawings. When the following description refers to the accompanying drawings, the same number in the different accompanying drawings represents the same or similar elements unless otherwise indicated. The implementations described in the following examples do not represent all implementations consistent with the disclosure. On the contrary, they are examples of an apparatus and method consistent with some aspects of the disclosure as detailed in the appended claims.

It is to be noted that all actions of obtaining a signal, information or data in the disclosure are performed under the premise of complying with the corresponding data protection regulations and policies of the local country, and with authorization of the corresponding apparatus owner.

The calculation of the heat consumption in the related art is not accurate enough. At present, there are the following several methods to estimate heat consumption, namely, calorie consumption, of a user in a motion process: a linear regression method based on a heart rate, a machine learning model or a deep learning model based on the heart rate, and heat consumption estimation based on acceleration. In the linear regression method based on the heart rate, a single linear regression model is usually used in the related art to estimate heat consumption of the user throughout the entire motion stage. However, an inventor has found through research that there is a strong linear relationship between the heart rate and a heat consumption during a motion steady-state stage, such as a process of running at a constant speed. However, in a motion recovery stage, and even in a case of motion at a variable speed, there is a clear non-linear relationship between the heart rate and the heat consumption. In the related art, the single linear regression model is used to estimate the heat consumption throughout the entire motion stage, without considering the motion stage where the user is currently located, which is usually not accurate. Especially in more complex motion scenarios such as cross-country running and mountaineering, a sporter often engages in a variable-speed motion with constantly changing motion intensity. The estimation of the heat consumption in such motion scenarios using the modes in the related art often has significant errors.

In view of this, the disclosure provides a heat consumption estimation method and apparatus, and a storage medium, so as to improve accuracy of estimating heat consumption of a user in the motion process. The implementations of the disclosure are illustrated in detail below.

It is to be noted that in one example, the heat consumption estimation method provided by the disclosure may be applied to a wearable device such as a smartwatch, and a smart bracelet. In a case that the user wears the wearable device, the wearable device can collect a heart rate of the user in real time and calculate the heat consumption of the user in the motion process. In another example, the heat consumption estimation method provided by the disclosure may be applied to a terminal that establishes a connection relationship with the wearable device, such as a phone, a tablet computer, and other devices of the user. The wearable device may transmit the collected heart rate of the user to the terminal in real time, and the terminal may obtain the heart rate of the user and calculate the heat consumption of the user in the motion process.

FIG. 1 is a flow diagram of a heat consumption estimation method shown according to an example. As shown in FIG. 1, the method may include S101 to S103.

In S101, a heart rate of a target user at a current moment is obtained.

The target user is a user wearing a wearable device, and the wearable device may collect the heart rate of the target user at a preset sampling frequency. For example, the preset sampling frequency is 1 HZ, and the wearable device may collect the heart rate of the target user every second.

In S102, motion state feature information of the target user at the current moment is determined. The motion state feature information is configured to represent whether the target user is in a motion steady-state stage or a motion recovery stage at the current moment.

The user usually goes through a motion initiation stage, a motion stabilization stage, and the motion recovery stage during the motion. The motion initiation stage refers to an initial stage of the motion, which is short in time and consumes less heat. The motion stabilization stage refers to a stage where breathing and the heart rate fluctuate less and are relatively stable, such as a stage of running at a constant speed. Due to the short time and less heat consumption of the motion initiation stage, in the disclosure, the motion initiation stage and the motion stabilization stage are taken as the motion steady-state stage. In outdoor long-distance running, cross-country running, mountaineering and other scenarios, a sporter will frequently run at a variable speed and take a short break to recover his/her energy. This stage of significantly reducing the speed or pausing the motion to recover the energy may be taken as the motion recovery stage.

Due to the different heart rates of the user at different motion stages, and the changes in heart rate with the motion stages, the motion state feature information of the target user at the current moment may be determined according to the heart rate at the current moment. In an optional example, a classifier model, such as a Bayesian classifier model, may be pre-trained to input the heart rate at the current moment into the classifier model, and the classifier model may output whether the target user is in the motion steady-state stage or the motion recovery stage at the current moment.

In S103, total heat consumption information of the target user in a motion process is determined according to the motion state feature information and the heart rate at the current moment.

At the motion recovery stage, the heart rate of the sporter is still at a high level, but the heat consumption at this point has gradually decreased. In the related art, the single linear regression model is used to estimate the heat consumption throughout the entire motion stage, without considering the motion stage where the user is currently located. This is usually manifested as overestimation of the heat consumption at the motion recovery stage, and the motion recovery stage is particularly common in complex motion scenarios such as outdoor long-distance running and mountaineering, leading to the constant accumulation of errors and a gradual decrease in the accuracy of heat consumption estimation. In the disclosure, the motion state feature information of the target user at the current moment is determined according to the heart rate of the target user at the current moment, and a heat consumption increment of the target user within a current time period is determined according to the motion state feature information, so as to determine total heat consumption information of the target user in the motion process. In the disclosure, in consideration of different characteristics of the heat consumption in the motion steady-state stage and the motion recovery stage, by considering which motion stage the target user is in, the estimation of the heat consumption can be more accurate.

The motion process includes a process from a motion starting moment to the current moment. For example, when getting ready to exercise, the target user may click a start motion button on the wearable device or the terminal, and may further select a type of the motion he/she is doing, such as jogging, mountaineering, and cross-country running. The moment when the target user triggers the start motion button may be used as the motion starting moment. In addition, the moment when the user wears the wearable device may also be used as the motion starting moment, even if the user does not click the start motion button, regardless of whether the user is in a motion state or a daily office state, the heat consumption of the user may be estimated. For example, the total heat consumption information may be represented by calorie.

Through the technical solution above, the heart rate of the target user at the current moment is obtained first, then the motion state feature information of the target user at the current moment is determined, the motion state feature information is configured to represent whether the target user is in the motion steady-state stage or the motion recovery stage at the current moment, and then the total heat consumption information of the target user in the motion process is determined according to the motion state feature information. Because there is a strong linear relationship between the heart rate and a heat consumption at the motion steady-state stage, but there is a clear non-linear relationship between the heart rate and the heat consumption at the motion recovery stage, at the motion recovery stage, the heart rate of the sporter is still at the high level, but the heat consumption at this point has gradually decreased. In the disclosure, in consideration of different characteristics of the heat consumption in the motion steady-state stage and the motion recovery stage, by considering which motion stage the target user is in, the estimation of the heat consumption can be more accurate.

Figure 2:
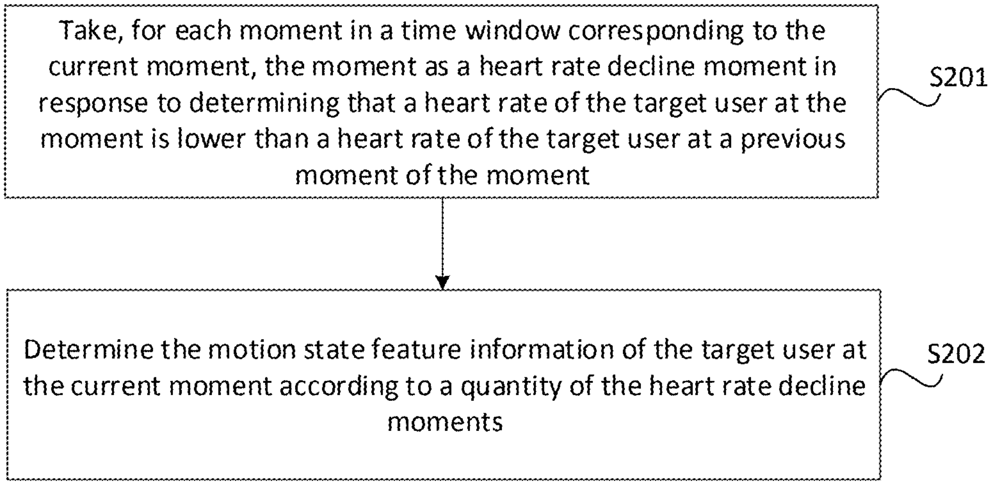
FIG. 2 is a flow diagram of a method for determining motion state feature information of a target user at a current moment shown according to an example.

FIG. 2 is a flow diagram of a method for determining the motion state feature information of the target user at the current moment shown according to an example. As shown in FIG. 2, S102 may include S201 and S202.

In S201, for each moment in a time window corresponding to the current moment, the moment is taken as a heart rate decline moment in response to determining that a heart rate of the target user at the moment is lower than a heart rate of the target user at a previous moment of the moment. The time window includes a time period from a specified moment to the current moment, and the specified moment is earlier than the current moment.

In S202, the motion state feature information of the target user at the current moment is determined according to a quantity of the heart rate decline moments.

In the motion process, when there is a significant decrease in the motion speed or a pause in motion to restore physical fitness, the heart rate shows a significant decline trend. However, the heart rate collected by the wearable device is jittery, and the heart rate does not strictly decrease at the motion recovery stage. A brief decline in the heart rate does not indicate that one is in the motion recovery stage, and when the heart rate maintains a continuous decline trend, it can indicate that one is in the motion recovery stage at the moment.

In the disclosure, a manner of sliding time window is adopted to detect whether the user is currently in the motion steady-state stage or the motion recovery stage. For example, taking thirty moments including t1, t2, t3, . . . , t28, t29, and t30 in sequence from front to back as an example for illustration, the current moment is for example the moment t30, a length of the time window may be pre-set, such as 30 seconds, and accordingly the specified moment may be the moment t1. For example, the length of the time window is set to be 20 seconds, and accordingly the specified moment may be the moment t10. The disclosure does not limit the length of the time window. Taking the specified moment being the moment t1 as an example, the time window corresponding to the current moment t30 includes a time period from t1 to t30.

It is worth noting that the wearable device collects the heart rate of the target user in real time. When obtaining the heart rate of the target user at the current moment, the wearable device or the terminal has already obtained a heart rate of the target user at each moment before the current moment. That is, when obtaining the heart rate of the target user at the moment t30, the wearable device or the terminal has already obtained the heart rate of the target user at the moments t1, t2, t3, . . . , t28, and t29 respectively.

In response to determining that the heart rate of the target user at the moment t30 is less the heart rate at the moment t29, the moment t30 may be taken as the heart rate decline moment. In response to determining that the heart rate of the target user at the moment t29 is less than the heart rate at the moment t28, then the moment t29 may be taken as the heart rate decline moment. In response to determining that the heart rate of the target user at the moment t28 is greater than or equal to the heart rate at the moment t27, the moment t28 is not taken as the heart rate decline moment, and the judgment of whether other moments are taken as the heart rate decline moment will not be repeated.

After determining which moments in the time window are taken as the heart rate decline moments, the motion state feature information of the target user at the current moment may be determined according to the quantity of the heart rate decline moments. The implementations of S202 above may be:

determining that the target user is in the motion recovery stage at the current moment in response to determining that the quantity of the heart rate decline moments meets at least one of preset conditions, where the preset conditions include: the quantity of the heart rate decline moments being greater than a preset quantity threshold, and a ratio between the quantity of the heart rate decline moments and a quantity of moments in the time window being greater than a preset ratio threshold.

The preset quantity threshold may be pre-set and may be set according to the length of the time window. For example, the length of the time window is 30 seconds, and the preset quantity threshold may be set to be 24. The preset ratio threshold may also be pre-set, for example, set to be 80%. In response to determining that the quantity of the heart rate decline moments meets at least one of the preset conditions, that is, in response to determining that one of the preset conditions is met or the two conditions are met simultaneously, it may represent that the heart rate of the target user within the time window continuously maintains the decline trend, and the current motion speed of the target user may significantly decrease or even the target user pauses the motion to recover the physical fitness, so that it may be determined that the target user is in the motion recovery stage at the current moment. In response to determining that the quantity of the heart rate decline moments is less than or equal to the preset quantity threshold, or the ratio between the quantity of the heart rate decline moments and the quantity of the moments in the time window is less than or equal to the preset ratio threshold, it may represent that the heart rate of the target user within the time window has not significantly decreased, and the target user does not slow down during the motion, so that it may be determined that the target user is in the motion steady-state stage at the current moment.

Through the technical solution above, the time window includes the time period from the specified moment to the current moment, and the specified moment is earlier than the current moment. The quantity of the heart rate decline moments in the time window may reflect whether the heart rate of the user is in a stable state or continuously maintains a decline trend in the recent time period, so as to accurately determine the motion state feature information of the target user at the current moment.

Figure 3:
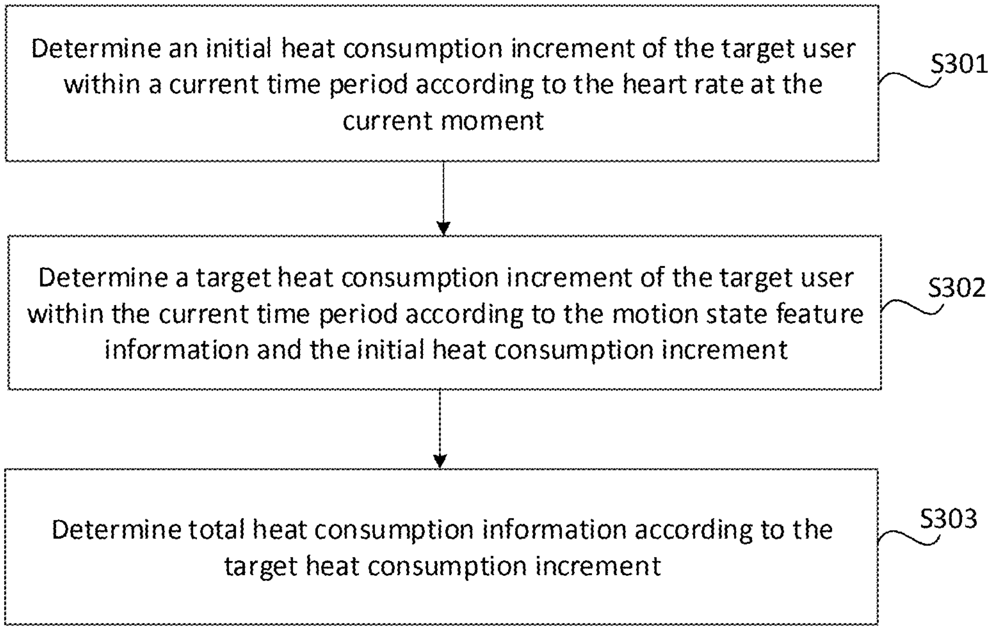
FIG. 3 is a flow diagram of a method for determining total heat consumption information of a target user in a motion process shown according to an example.

FIG. 3 is a flow diagram of a method for determining the total heat consumption information of the target user in the motion process shown according to an example. As shown in FIG. 3, S103 may include S301 to S303.

In S301, an initial heat consumption increment of the target user within a current time period is determined according to the heart rate at the current moment.

The current time period is a time period from a previous moment of the current moment to the current moment. Continuing to use the above moment example, for example, the current moment is the moment t30, and the current time period is a time period from the moment t29 to the moment t30, and the heat consumption increment within the current time period is the heat consumption of the target user from the moment t29 to the moment t30.

Figure 4:
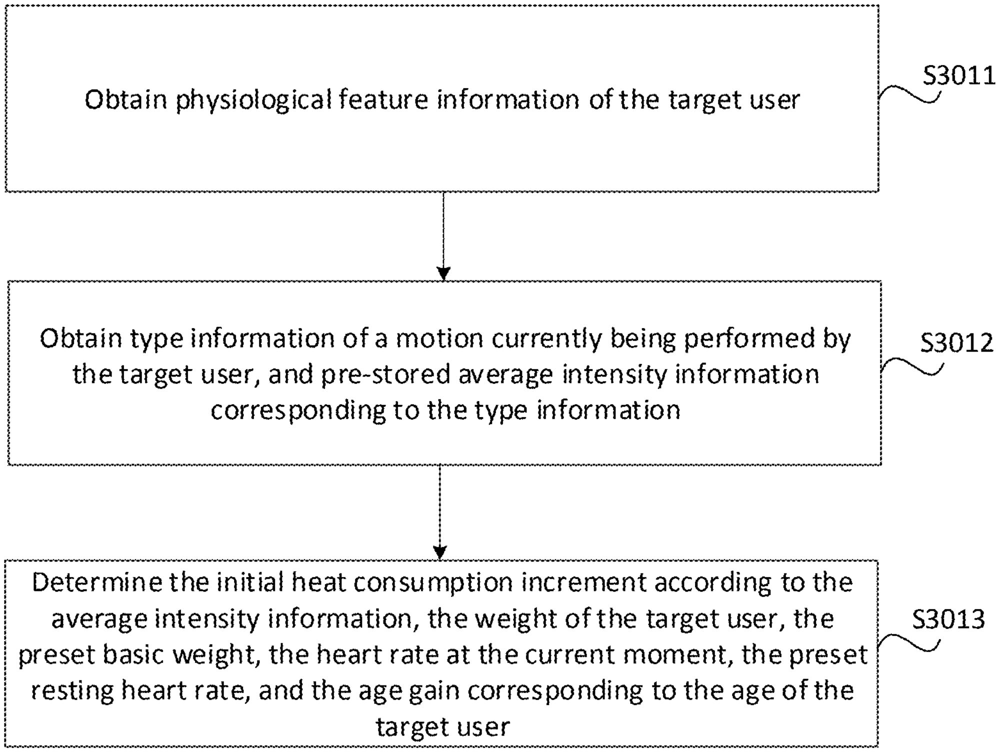
FIG. 4 is a flow diagram of a method for determining an initial heat consumption increment of a target user within a current time period shown according to an example.

In one example, the implementation of S301 may be shown in FIG. 4, including S3011 to S3013.

In S3011, physiological feature information of the target user is obtained. The physiological feature information of the target user includes a weight and an age of the target user.

When estimating heat consumption in the related art, the problem of individual difference is not considered. Different users may consume different amounts of heat even during the same motion. When the human body is exercising, there are multiple factors that affect the heat consumption. For example, to complete the same motion, heavier users need to do more external work, and the weight has a significant impact on the heat consumption. In addition, the age may affect a metabolic rate of the body, which may also affect the heat consumption during the motion.

In the disclosure, when estimating the heat consumption, the physiological feature information of the user is considered, the physiological feature information, for example, includes the weight and the age of the user, that is, the problem of individual difference is considered, which can reduce the individual difference in heat consumption estimation and make the heat consumption estimation more accurate.

It is to be noted that the target user may fill in his/her weight and age on the wearable device or the terminal, and with the user authorization, the wearable device or the terminal may obtain the weight and the age of the target user.

In S3012, type information of a motion currently being performed by the target user, and pre-stored average intensity information corresponding to the type information are obtained.

In one example, when getting ready to exercise, the target user may click the start motion button on the wearable device or the terminal, and may further select a type of the motion he/she is doing, such as jogging, mountaineering, and cross-country running. According to a selection operation of the target user, the wearable device or the terminal may obtain the type information of the motion currently being performed by the target user. In another example, the wearable device or the terminal may determine the type information of the motion currently being performed by the target user according to a heart rate change feature of the target user. For example, in response to determining that the heart rate of the target user fluctuates gently, the target user may perform a constant speed motion currently, such as running on a treadmill. In response to determining that the heart rate of the target user fluctuates strongly, the target user may perform a variable speed motion currently, such as mountaineering and cross-country running. The wearable device or the terminal may pre-store average intensity information respectively corresponding to various motions, such as average intensity information A1 for jogging, average intensity information A2 for mountaineering, average intensity information A3 for cross-country running, and average intensity information A4 for cycling.

In one example, the average intensity information corresponding to the type information may be obtained through the following modes:

obtaining physiological feature information of a motion user who performs a motion corresponding to the type information, and a motion heart rate and an actual heat consumption increment of the motion user during the motion steady-state stage; and fitting the average intensity information according to the actual heat consumption increment, the motion heart rate, a preset resting heart rate, a weight of the motion user, a preset basic weight, and an age gain corresponding to an age of the motion user.

In the disclosure, a model between the heart rate and the heat consumption increment is established in combination with a physiological characteristic of high linear correlation between the heart rate and the heat consumption during the steady-state motion. For example, by fitting the average intensity information of jogging, the motion heart rate and the actual heat consumption increment of the motion user who jogs during the motion steady-state stage may be collected. The actual heat consumption increment may be calculated using a professional cardiopulmonary function testing system through gas exchange, namely, the heat consumption of the motion user within a collection cycle (such as 1 second) for collecting the motion heart rate. In order to reduce the individual difference, the physiological feature information of the motion user may further be obtained, and the physiological feature information includes the weight and the age of the motion user. A large amount of information on the motion user who jogs may be collected to make the fitted average intensity information more accurate.

To reduce the individual differences, normalized parameters may be used when establishing the model. The ratio between the weight of the motion user and the preset basic weight may be taken as a weight gain multiplier, and the preset basic weight may be pre-set, for example, set to be 60 kg. The difference between the motion heart rate and the preset resting heart rate may be taken as a heart rate increment, and the preset resting heart rate may also be pre-set. The age gain refers to a change in metabolic rate corresponding to an age change according to a physiological basis of the human body, is an empirical value, and ranges from 0.95 to 1.12. The age gain may be set as a fixed value within this range.

For example, the average intensity information may be fitted through the following model (1):

$$\text{Calories\_delta}' = A * \text{weight\_multiple}' * \text{hr\_add}' * \text{age\_gain}' \quad (1)$$

where, Calories_delta' is the actual heat consumption increment, A is the average intensity information, weight_multiple'=weight'/weight_basic, weight' is the weight of the motion user, weight_basic is the preset basic weight, hr_add'=hr'−hr_rest, hr' is the motion heart rate, hr_rest is the preset resting heart rate, and age_gain' is the age gain corresponding to the age of the motion user. When fitting the average intensity information, Calories_delta', weight_multiple', hr_add', and age_gain' are all known, and the average intensity information A may be fitted through the model (1). The manner of fitting the average intensity information of other types of motion is similar.

In S3013, the initial heat consumption increment is determined according to the average intensity information, the weight of the target user, the preset basic weight, the heart rate at the current moment, the preset resting heart rate, and the age gain corresponding to the age of the target user.

For example, the initial heat consumption increment Calories_delta may be determined through the following model (2):

$$\text{Calories\_delta} = A * \text{weight\_multiple} * \text{hr\_add} * \text{age\_gain} \quad (2)$$

where, weight_multiple=weight/weight_basic, weight is the weight of the target user, weight_basic is the preset basic weight, hr_add=hr−hr_rest, hr is the heart rate at the current moment, hr_rest is the preset resting heart rate, and age_gain is the age gain corresponding to the age of the target user. When determining the initial heat consumption increment Calories_delta, A, weight_multiple, hr_add, and age_gain are all known, and the initial heat consumption increment is determined from this.

In S302, a target heat consumption increment of the target user within the current time period is determined according to the motion state feature information and the initial heat consumption increment.

The implementation of step S302 may be as follows:

taking the initial heat consumption increment as the target heat consumption increment in response to determining that the motion state feature information represents that the target user is in the motion steady-state stage at the current moment; and determining, in response to determining that the motion state feature information represents that the target user is in the motion recovery stage at the current moment, the target heat consumption increment according to the initial heat consumption increment, the heart rate at the current moment, a maximum heart rate in the motion process, and the preset resting heart rate.

In response to determining that the target user is currently in the motion steady-state stage, there is a linear relationship between the heart rate and the heat consumption during the motion steady-state stage. The initial heat consumption increment determined according to the model (1) is accurate and may be taken as the target heat consumption increment of the target user in the current time period.

In response to determining that the target user is currently in the motion recovery stage, due to the presence of excess post-exercise oxygen consumption (EPOC), the rate of energy consumption at the motion recovery stage will be higher than the basal metabolism at rest, but lower than that at the motion steady-state stage. Although the heart rate at the motion recovery stage may decrease, it still remains at a high level. At this time, although the heart rate is at the high level, the heat consumption has decreased, and there is a non-linear relationship between the heart rate and the heat consumption. Directly using the initial heat consumption increment determined by the model (1) at the motion recovery stage may lead to a problem of overestimation of heat consumption prediction.

Figure 5:
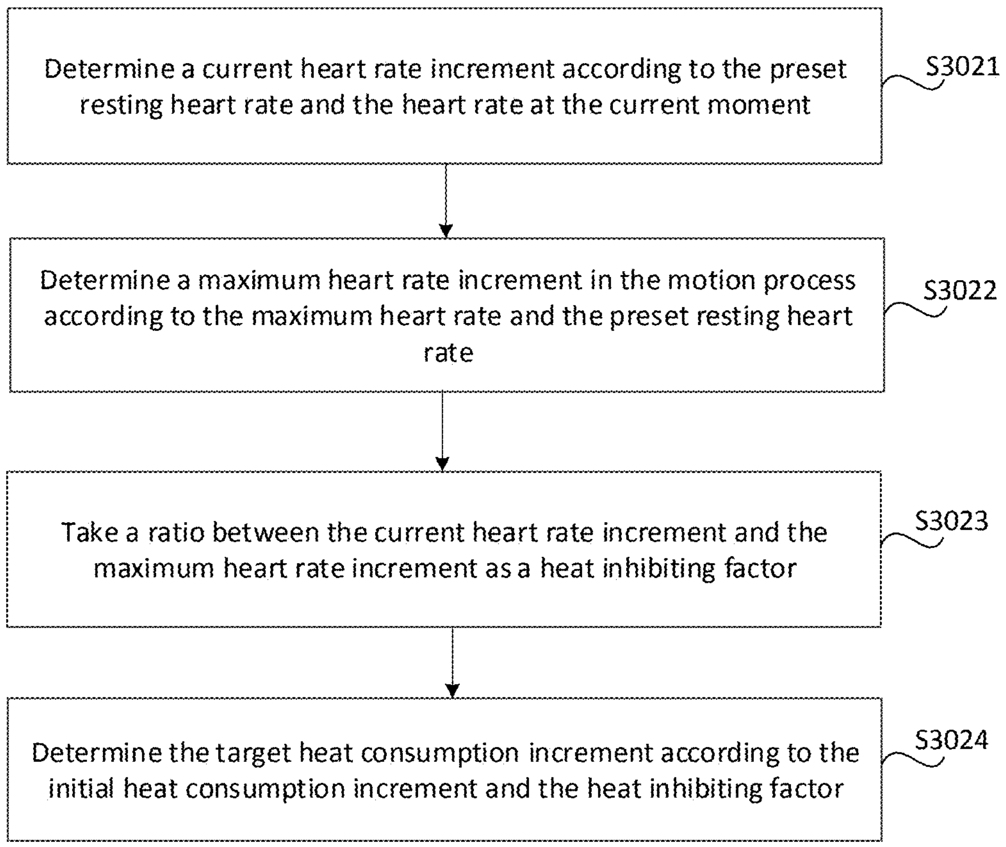
FIG. 5 is a flow diagram of a method for determining a target heat consumption increment at a motion recovery stage shown according to an example.

In the disclosure, in order to make the heat consumption estimation at the motion recovery stage more accurate, in response to determining that the target user is currently in the motion recovery stage, the target heat consumption increment is determined according to the initial heat consumption increment, the heart rate at the current moment, the maximum heart rate in the motion process, and the preset resting heart rate. The manner of determining the target heat consumption increment at the motion recovery stage may be shown in FIG. 5, including S3021 to S3024.

In S3021, a current heart rate increment is determined according to the preset resting heart rate and the heart rate at the current moment.

For example, a difference value between the heart rate at the current moment and the preset resting heart rate may be taken as the current heart rate increment.

In S3022, a maximum heart rate increment in the motion process is determined according to the maximum heart rate and the preset resting heart rate.

For example, a difference value between the maximum heart rate in the motion process and the preset resting heart rate may be taken as the maximum heart rate increment.

In S3023, a ratio between the current heart rate increment and the maximum heart rate increment is taken as a heat inhibiting factor.

The heat inhibiting factor η may be determined through the following formula (3):

$$\eta = \frac{\text{hr} - \text{hr\_rest}}{\text{hr\_max} - \text{hr\_rest}} \quad (3)$$

where, hr is the heart rate at the current moment, hr_rest is the preset resting heart rate, and hr_max is the maximum heart rate in the motion process.

In S3024, the target heat consumption increment is determined according to the initial heat consumption increment and the heat inhibiting factor.

For example, a product of the initial heat consumption increment and the heat inhibiting factor may be taken as the target heat consumption increment.

The above maximum heart rate in the motion process is updated in real time in the motion process. In this way, by using the heat inhibiting factor, a strategy is made to inhibit the heat consumption increment at the motion recovery stage, which can avoid the overestimation of the heat consumption at the motion recovery stage and improve the accuracy of the heat consumption estimation.

In S303, total heat consumption information is determined according to the target heat consumption increment.

For example, the current moment is the moment t30, at the current moment, the total heat consumption of the target user from the motion starting moment to the moment t29 has been calculated. By adding the target heat consumption increment to the total heat consumption of the target user from the motion starting moment to the moment t29, the total heat consumption information of the target user from the motion starting moment to the current moment may be obtained.

Through the technical solution above, the model, that considers the individual physiological difference, between the heart rate and the heat consumption is established. This model can reduce the individual difference in heat consumption estimation and make the heat consumption estimation more accurate. In addition, at the motion recovery stage, the heart rate still remains at a high level, but at this point, the heat consumption has gradually decreased. In this way, by using the heat inhibiting factor, a strategy is made to inhibit the heat consumption increment at the motion recovery stage, which can avoid the overestimation of the heat consumption at the motion recovery stage and improve the accuracy of the heat consumption estimation at the motion recovery stage.

The heat consumption estimation method provided by the disclosure may further include:

- determining, after the target user finishes the motion, current basal metabolism information of the target user according to a heat consumption of the target user during this motion, and displaying the current basal metabolism information, where the current basal metabolism information is greater than basal metabolism information of the target user before this motion.

Basal metabolism refers to energy metabolism in a basic state of the human body. The motion may improve the basal metabolism of the human body. The higher the intensity of the motion, the higher the amount of the heat consumed, and the higher the level of basal metabolism improvement. After the target user finishes the motion, the current basal metabolism information of the target user may be determined according to the heat consumption of the target user during this motion, and displayed on the wearable device or the terminal. The manner of calculating the basal metabolism information may refer to the related art. For example, a coefficient is determined according to the heat consumption of the target user during this motion, and original basal metabolism information is multiplied with this coefficient to obtain the current basal metabolism information. Due to the fact that the motion may improve the basal metabolism level of the human body, the current basal metabolism information of the target user after this motion is greater than the basal metabolism information of the target user before this motion.

Figure 6:
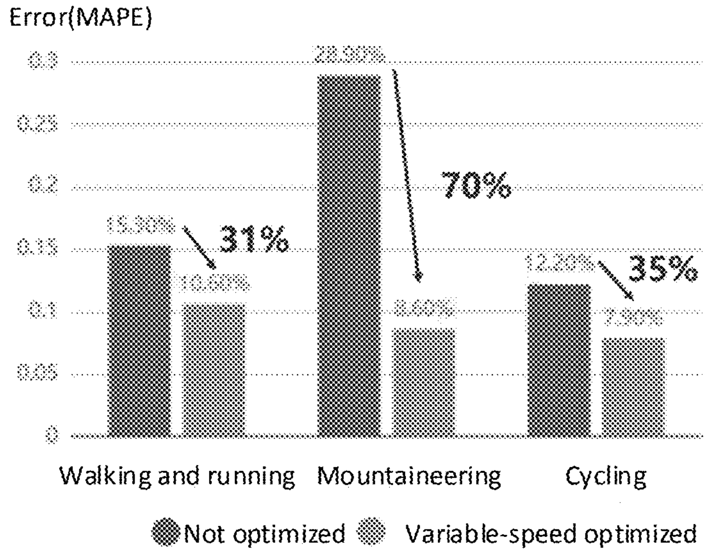
FIG. 6 is a schematic diagram of an experimental result for heat consumption estimation.

FIG. 6 is a schematic diagram of an experimental result for heat consumption estimation. In the experiment, 100 pieces of motion data for motion types of walking and running (including indoor walking, indoor running, outdoor walking, and outdoor running) were collected, and a motion time length contains three levels of 10 minutes, 30 minutes, and 60 minutes. 20 pieces of motion data for the motion type of mountaineering were collected, including five peaks of different heights, and a motion time length ranges from 20 minutes to 180 minutes. 40 pieces of motion data for the motion type of cycling were collected, including four different cycling venues, and involving professional cycling venues and non-professional cycling roads (such as outdoor roads). The age of subjects in the above experiment ranges from 18 years old to 43 years old.

As shown in FIG. 6, in the scenario where the motion type is walking and running, an average error of the calculated heat consumption without motion recovery stage detection is 15.30%. The motion recovery stage is detected using the method in the disclosure, the heat consumption is optimized and adjusted by the heat inhibiting factor, an average error of the optimized algorithm is 10.60%, and estimation precision is improved by 31%. In the scenario where the motion type is mountaineering, an average error of the calculated heat consumption without motion recovery stage detection is 28.90%. The motion recovery stage is detected using the method in the disclosure, the heat consumption is optimized and adjusted by the heat inhibiting factor, an average error of the optimized algorithm is 8.60%, and estimation precision is improved by 70%. In the scenario where the motion type is cycling, an average error of the calculated heat consumption without motion recovery stage detection is 12.20%. The motion recovery stage is detected using the method in the disclosure, the heat consumption is optimized and adjusted by the heat inhibiting factor, an average error of the optimized algorithm is 7.90%, and estimation precision is improved by 35%.

Figure 7:
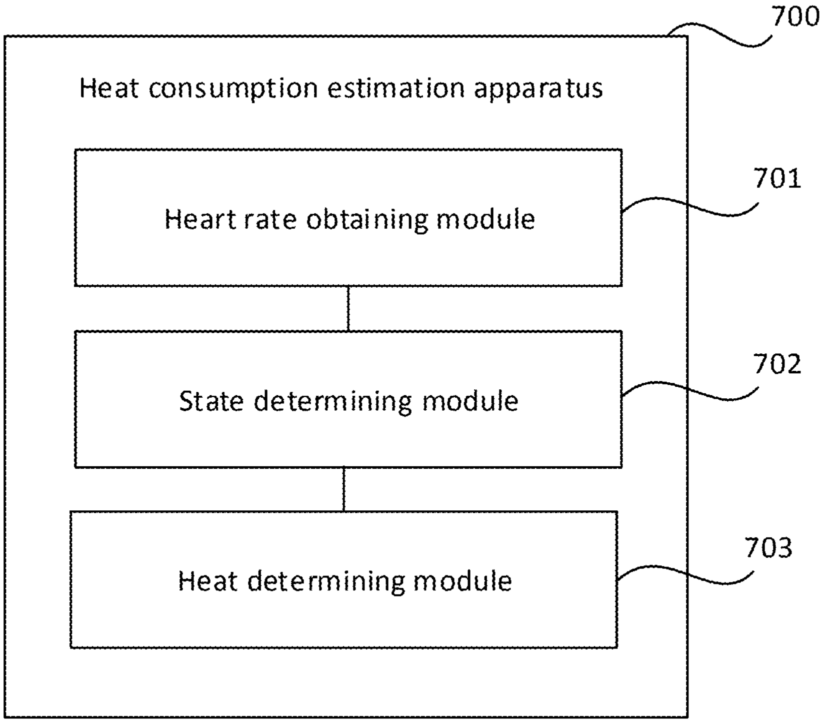
FIG. 7 is a block diagram of a heat consumption estimation apparatus shown according to an example.

Based on the same invention concept, the disclosure further provides a heat consumption estimation apparatus. FIG. 7 is a block diagram of a heat consumption estimation apparatus shown according to an example. As shown in FIG. 7, the apparatus 700 may include:

- a heart rate obtaining module 701, configured to obtain a heart rate of a target user at a current moment;
- a state determining module 702, configured to determine motion state feature information of the target user at the current moment, where the motion state feature information is configured to represent whether the target user is in a motion steady-state stage or a motion recovery stage at the current moment; and
- a heat determining module 703, configured to determine, according to the motion state feature information and the heart rate at the current moment, total heat consumption information of the target user in a motion process, where the motion process includes a process from a motion starting moment to the current moment.

In some examples, the state determining module 702 includes:

- a heart rate decline moment determining submodule, configured to take, for each moment in a time window corresponding to the current moment, the moment as a heart rate decline moment in response to determining that a heart rate of the target user at the moment is lower than a heart rate of the target user at a previous moment of the moment, where the time window includes a time period from a specified moment to the current moment, and the specified moment is earlier than the current moment; and
- a state determining submodule, configured to determine the motion state feature information of the target user at the current moment according to the quantity of the heart rate decline moments.

In some examples, the state determining submodule is configured to determine that the target user is in the motion recovery stage at the current moment in response to determining that the quantity of the heart rate decline moments meets at least one of preset conditions, where the preset conditions include: the quantity of the heart rate decline moments being greater than a preset quantity threshold, and a ratio between the quantity of the heart rate decline moments and the quantity of moments in the time window being greater than a preset ratio threshold.

In some examples, the heat determining module 703 includes:

a first determining submodule, configured to determine an initial heat consumption increment of the target user within a current time period according to the heart rate at the current moment, where the current time period is a time period from a previous moment of the current moment to the current moment;

a second determining submodule, configured to determine a target heat consumption increment of the target user within the current time period according to the motion state feature information and the initial heat consumption increment; and a third determining submodule, configured to determine the total heat consumption information according to the target heat consumption increment.

In some examples, the first determining submodule includes:

a first obtaining submodule, configured to obtain physiological feature information of the target user, where the physiological feature information of the target user includes a weight and an age of the target user;

a second obtaining submodule, configured to obtain type information of a motion currently being performed by the target user, and pre-stored average intensity information corresponding to the type information; and a fourth determining submodule, configured to determine the initial heat consumption increment according to the average intensity information, the weight of the target user, a preset basic weight, the heart rate at the current moment, a preset resting heart rate, and an age gain corresponding to the age of the target user.

In some examples, the average intensity information corresponding to the type information is obtained through the following modules:

an information obtaining module, configured to obtain physiological feature information of a motion user who performs the motion corresponding to the type information, and a motion heart rate and an actual heat consumption increment of the motion user during the motion steady-state stage, where the physiological feature information of the motion user includes a weight and an age of the motion user; and a fitting module, configured to fit the average intensity information according to the actual heat consumption increment, the motion heart rate, the preset resting heart rate, the weight of the motion user, the preset basic weight, and an age gain corresponding to the age of the motion user.

In some examples, the second determining submodule includes:

a fifth determining submodule, configured to take the initial heat consumption increment as the target heat consumption increment in response to determining that the motion state feature information represents that the target user is in the motion steady-state stage at the current moment; and a sixth determining submodule, configured to determine, in response to determining that the motion state feature information represents that the target user is in the motion recovery stage at the current moment, the target heat consumption increment according to the initial heat consumption increment, the heart rate at the current moment, a maximum heart rate in the motion process, and the preset resting heart rate.

In some examples, the sixth determining submodule includes:

a current heart rate increment determining submodule, configured to determine a current heart rate increment according to the preset resting heart rate and the heart rate at the current moment;

a maximum heart rate increment determining submodule, configured to determine a maximum heart rate increment in the motion process according to the maximum heart rate and the preset resting heart rate;

a heat inhibiting factor determining submodule, configured to take a ratio between the current heart rate increment and the maximum heart rate increment as a heat inhibiting factor; and a heat consumption increment determining submodule, configured to determine the target heat consumption increment according to the initial heat consumption increment and the heat inhibiting factor.

In some examples, the apparatus 700 further includes:

a basal metabolism determining module, configured to determine, after the target user finishes the motion, current basal metabolism information of the target user according to a heat consumption of the target user during this motion, and display the current basal metabolism information, where the current basal metabolism information is greater than basal metabolism information of the target user before this motion.

As for the apparatus in the above examples, the specific modes for executing operations by all the modules have been described in the examples related to the method in detail, which are not illustrated in detail here.

The disclosure further provides a non-transitory computer readable storage medium, storing a computer program instruction. The computer program instruction, when executed by a processor, implements steps of the heat consumption estimation method provided by the disclosure.

Figure 8:
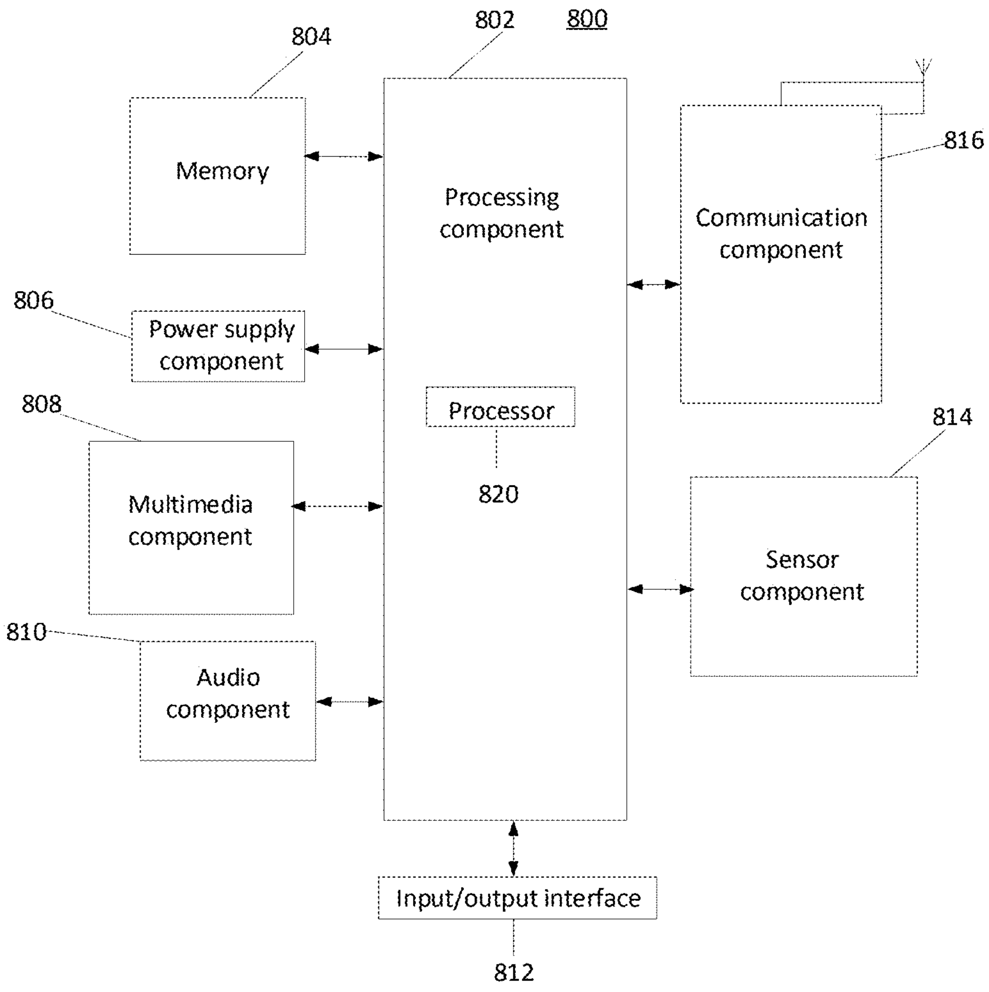
FIG. 8 is a block diagram of an apparatus for heat consumption estimation shown according to an example.

FIG. 8 is a block diagram of an apparatus 800 for heat consumption estimation shown according to an example. For example, the apparatus 800 may be a mobile telephone, a computer, a digital broadcast terminal, a message transceiving device, a game console, a tablet device, a medical device, a fitness device, a personal digital assistant, and the like.

Referring to FIG. 8, the apparatus 800 may include one or more of the following components: a processing component 802, a memory 804, a power supply component 806, a multimedia component 808, an audio component 810, an input/output (I/O) interface 812, a sensor component 814, and a communication component 816.

The processing component 802 usually controls an overall operation of the apparatus 800, such as operations associated with displaying, telephone calling, data communication, a camera operation and a record operation. The processing component 802 may include one or more processors 820 to execute an instruction, so as to complete all or part of steps of the heat consumption estimation method above. In addition, the processing component 802 may include one or more modules, so as to facilitate interaction between the processing component 802 and other components. For example, the processing component 802 may include a multimedia module, so as to facilitate interaction between the multimedia component 808 and the processing component 802.

The memory 804 is configured to store various types of data so as to support operations on the apparatus 800. Examples of these data include instructions of any application program or method used to be operated on the apparatus 800, contact data, telephone directory data, messages, pictures, videos, and the like. The memory 804 may be implemented by any type of volatile or nonvolatile storage device or their combinations, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic disk or an optical disk.

The power supply component 806 provides electric power for various components of the apparatus 800. The power supply component 806 may include a power management system, one or more power sources, and other components associated with generating, managing and distributing electric power for the apparatus 800.

The multimedia component 808 includes a screen providing an output interface between the apparatus 800 and a user. In some examples, the screen may include a liquid crystal display (LCD) and a touch panel (TP). In response to determining that the screen includes the touch panel, the screen may be implemented as a touch screen so as to receive an input signal from the user. The touch panel includes one or more touch sensors to sense touching, swiping and gestures on the touch panel. The touch sensor may not only sense a boundary of a touching or swiping action, but also detect duration and pressure related to the touching or swiping operation. In some examples, the multimedia component 808 includes a front camera and/or a back camera. In response to determining that the apparatus 800 is in an operation mode, such as a shooting mode or a video mode, the front camera and/or the back camera may receive external multimedia data. Each front camera and each back camera may be a fixed optical lens system or have a focal length and optical zooming capability.

The audio component 810 is configured to output and/or input an audio signal. For example, the audio component 810 includes a microphone (MIC). When the apparatus 800 is in an operation mode, such as a call mode, a recording mode or a speech recognition mode, the microphone is configured to receive an external audio signal. The received audio signal may be further stored in the memory 804 or sent via the communication component 816. In some examples, the audio component 810 further includes a speaker for outputting the audio signal.

The I/O interface 812 provides an interface between the processing component 802 and a peripheral interface module, and the above peripheral interface module may be a keyboard, a click wheel, buttons, etc. These buttons may include but are not limited to: a home button, a volume button, a start button and a lock button.

The sensor component 814 includes one or more sensors for providing state evaluations of all aspects for the apparatus 800. For example, the sensor component 814 may detect an on/off state of the apparatus 800 and relative positioning of components, for example, the components are a display and a keypad of the apparatus 800. The sensor component 814 may further detect location change of the apparatus 800 or one component of the apparatus 800, whether there is a contact between the user and the apparatus 800, azimuth or speed up/speed down of the apparatus 800, and temperature change of the apparatus 800. The sensor component 814 may include a proximity sensor, which is configured to detect existence of a nearby object without any physical contact. The sensor component 814 may further include an optical sensor, such as a CMOS or CCD image sensor, for use in an imaging application. In some examples, the sensor component 814 may further include an acceleration sensor, a gyroscope sensor, a magnetic sensor, a pressure sensor or a temperature sensor.

The communication component 816 is configured to facilitate wired or wireless communication between the apparatus 800 and other devices. The apparatus 800 may access a wireless network based on a communication standard, such as WiFi, 2G or 3G, or their combinations. In one example, the communication component 816 receives a broadcast signal or broadcast related information from an external broadcast management system via a broadcast channel. In an example, the communication component 816 further includes a near-field communication (NFC) module so as to facilitate short-range communication. For example, the NFC module may be implemented based on a radio frequency identification (RFID) technology, an infrared data association (IrDA) technology, an ultra wide band (UWB) technology, a Bluetooth (BT) technology and other technologies.

In an example, the apparatus 800 may be implemented by one or more application specific integrated circuits (ASICs), digital signal processors (DSPs), digital signal processing devices (DSPDs), programmable logic devices (PLDs), field-programmable gate arrays (FPGAs), controllers, microcontrollers, microprocessors or other electronic elements for executing the heat consumption estimation method above.

In an example, a non-transitory computer readable storage medium including instructions is further provided, such as a memory 804 including instructions. The above instructions may be executed by the processor 820 of the apparatus 800 so as to complete the heat consumption estimation method above. For example, the non-transitory computer readable storage medium may be an ROM, a random access memory (RAM), a CD-ROM, a magnetic tape, a floppy disk, an optical data storage device and the like.

In another example, a computer program product is further provided, containing a computer program executable by a programmable apparatus. The computer program has, when executed by the programmable apparatus, a code section for executing the heat consumption estimation method above.

Those skilled in the art will easily figure out other implementation solutions of the disclosure after considering the specification and practicing the disclosure. The disclosure intends to cover any variations, usage or adaptive change of the disclosure, and these variations, usages or adaptive changes conform to a general principle of the disclosure and include common general knowledge or customary technical means in the technical field not disclosed by the disclosure. The specification and the examples are regarded as being for example.

It is to be understood that the disclosure is not limited to the exact structure that has been described above and shown in the accompanying drawings, and various modifications and changes may be made without departing from the scope of the disclosure. The scope of the disclosure is limited by the appended claims.

The invention claimed is:

1. A heat consumption estimation method, comprising:

obtaining a heart rate of a target user at a current moment;

determining motion state feature information of the target user at the current moment, wherein the motion state feature information is configured to represent whether the target user is in a motion steady-state stage or a motion recovery stage at the current moment; and determining, according to the motion state feature information and the heart rate at the current moment, total heat consumption information of the target user in a motion process, wherein the motion process comprises a process from a motion starting moment to the current moment;

wherein determining the motion state feature information of the target user at the current moment comprises:

taking, for each moment in a time window corresponding to the current moment, the moment as a heart rate decline moment in response to determining that a heart rate of the target user at the moment is lower than a heart rate of the target user at a previous moment of the moment, wherein the time window comprises a time period from a specified moment to the current moment, and the specified moment is earlier than the current moment; and determining the motion state feature information of the target user at the current moment according to a quantity of the heart rate decline moments;

wherein determining, according to the motion state feature information and the heart rate at the current moment, the total heat consumption information of the target user in the motion process comprises:

determining an initial heat consumption increment of the target user within a current time period according to the heart rate at the current moment, wherein the current time period is a time period from a previous moment of the current moment to the current moment;

determining a target heat consumption increment of the target user within the current time period according to the motion state feature information and the initial heat consumption increment; and determining the total heat consumption information according to the target heat consumption increment.

2. The heat consumption estimation method according to claim 1, wherein determining the motion state feature information of the target user at the current moment according to the quantity of the heart rate decline moments comprises:

determining that the target user is in the motion recovery stage at the current moment in response to determining that the quantity of the heart rate decline moments meets at least one of preset conditions, wherein the preset conditions comprise: the quantity of the heart rate decline moments being greater than a preset quantity threshold, and a ratio between the quantity of the heart rate decline moments and a quantity of moments in the time window being greater than a preset ratio threshold.

3. The heat consumption estimation method according to claim 1, wherein determining the initial heat consumption increment of the target user within the current time period according to the heart rate at the current moment comprises:

obtaining physiological feature information of the target user, wherein the physiological feature information of the target user comprises a weight and an age of the target user;

obtaining type information of a motion currently being performed by the target user, and pre-stored average intensity information corresponding to the type information; and determining the initial heat consumption increment according to the average intensity information, the weight of the target user, a preset basic weight, the heart rate at the current moment, a preset resting heart rate, and an age gain corresponding to the age of the target user.

4. The heat consumption estimation method according to claim 3, wherein the average intensity information corresponding to the type information is obtained through the following modes:

obtaining physiological feature information of a motion user who performs a motion corresponding to the type information, and a motion heart rate and an actual heat consumption increment of the motion user during the motion steady-state stage, wherein the physiological feature information of the motion user comprises a weight and an age of the motion user; and fitting the average intensity information according to the actual heat consumption increment, the motion heart rate, the preset resting heart rate, the weight of the motion user, the preset basic weight, and an age gain corresponding to the age of the motion user.

5. The heat consumption estimation method according to claim 1, wherein determining the target heat consumption increment of the target user within the current time period according to the motion state feature information and the initial heat consumption increment comprises:

taking the initial heat consumption increment as the target heat consumption increment in response to determining that the motion state feature information represents that the target user is in the motion steady-state stage at the current moment; and determining, in response to determining that the motion state feature information represents that the target user is in the motion recovery stage at the current moment, the target heat consumption increment according to the initial heat consumption increment, the heart rate at the current moment, a maximum heart rate in the motion process, and a preset resting heart rate.

6. The heat consumption estimation method according to claim 5, wherein determining the target heat consumption increment according to the initial heat consumption increment, the heart rate at the current moment, the maximum heart rate in the motion process, and the preset resting heart rate comprises:

determining a current heart rate increment according to the preset resting heart rate and the heart rate at the current moment;

determining a maximum heart rate increment in the motion process according to the maximum heart rate and the preset resting heart rate;

taking a ratio between the current heart rate increment and the maximum heart rate increment as a heat inhibiting factor; and determining the target heat consumption increment according to the initial heat consumption increment and the heat inhibiting factor.

7. The heat consumption estimation method according to claim 1, further comprising:

determining, after the target user finishes the motion, current basal metabolism information of the target user according to a heat consumption of the target user during this motion, and displaying the current basal metabolism information, wherein the current basal metabolism information is greater than basal metabolism information of the target user before this motion.

8. A heat consumption estimation apparatus, comprising:

one or more processors; and a memory storing processor-executable instructions;

wherein the processor-executable instructions, when executed by the one or more processors, cause the heat consumption estimation apparatus to:

obtain a heart rate of a target user at a current moment;

determine motion state feature information of the target user at the current moment, wherein the motion state feature information is configured to represent whether the target user is in a motion steady-state stage or a motion recovery stage at the current moment; and determine, according to the motion state feature information and the heart rate at the current moment, total heat consumption information of the target user in a motion process, wherein the motion process comprises a process from a motion starting moment to the current moment;

wherein the processor-executable instructions, when executed by the one or more processors, further cause the heat consumption estimation apparatus to:

take, for each moment in a time window corresponding to the current moment, the moment as a heart rate decline moment in response to determining that a heart rate of the target user at the moment is lower than a heart rate of the target user at a previous moment of the moment, wherein the time window comprises a time period from a specified moment to the current moment, and the specified moment is earlier than the current moment; and determine the motion state feature information of the target user at the current moment according to a quantity of the heart rate decline moments;

wherein the processor-executable instructions, when executed by the one or more processors, further cause the heat consumption estimation apparatus to:

determine an initial heat consumption increment of the target user within a current time period according to the heart rate at the current moment, wherein the current time period is a time period from a previous moment of the current moment to the current moment;

determine a target heat consumption increment of the target user within the current time period according to the motion state feature information and the initial heat consumption increment; and determine the total heat consumption information according to the target heat consumption increment.

9. The heat consumption estimation apparatus according to claim 8, wherein the processor-executable instructions, when executed by the one or more processors, further cause the heat consumption estimation apparatus to:

determine that the target user is in the motion recovery stage at the current moment in response to determining that the quantity of the heart rate decline moments meets at least one of preset conditions, wherein the preset conditions comprise: the quantity of the heart rate decline moments being greater than a preset quantity threshold, and a ratio between the quantity of the heart rate decline moments and a quantity of moments in the time window being greater than a preset ratio threshold.

10. The heat consumption estimation apparatus according to claim 8, wherein the processor-executable instructions, when executed by the one or more processors, further cause the heat consumption estimation apparatus to:

obtain physiological feature information of the target user, wherein the physiological feature information of the target user comprises a weight and an age of the target user;

obtain type information of a motion currently being performed by the target user, and pre-stored average intensity information corresponding to the type information; and determine the initial heat consumption increment according to the average intensity information, the weight of the target user, a preset basic weight, the heart rate at the current moment, a preset resting heart rate, and an age gain corresponding to the age of the target user.

11. The heat consumption estimation apparatus according to claim 10, wherein the processor-executable instructions, when executed by the one or more processors, further cause the heat consumption estimation apparatus to:

obtain the average intensity information corresponding to the type information through the following modes:

obtain physiological feature information of a motion user who performs a motion corresponding to the type information, and a motion heart rate and an actual heat consumption increment of the motion user during the motion steady-state stage, wherein the physiological feature information of the motion user comprises a weight and an age of the motion user; and fit the average intensity information according to the actual heat consumption increment, the motion heart rate, the preset resting heart rate, the weight of the motion user, the preset basic weight, and an age gain corresponding to the age of the motion user.

12. The heat consumption estimation apparatus according to claim 8, wherein the processor-executable instructions, when executed by the one or more processors, further cause the heat consumption estimation apparatus to:

take the initial heat consumption increment as the target heat consumption increment in response to determining that the motion state feature information represents that the target user is in the motion steady-state stage at the current moment; and determine, in response to determining that the motion state feature information represents that the target user is in the motion recovery stage at the current moment, the target heat consumption increment according to the initial heat consumption increment, the heart rate at the current moment, a maximum heart rate in the motion process, and a preset resting heart rate.

13. The heat consumption estimation apparatus according to claim 12, wherein the processor-executable instructions, when executed by the one or more processors, further cause the heat consumption estimation apparatus to:

determine a current heart rate increment according to the preset resting heart rate and the heart rate at the current moment;

determine a maximum heart rate increment in the motion process according to the maximum heart rate and the preset resting heart rate;

take a ratio between the current heart rate increment and the maximum heart rate increment as a heat inhibiting factor; and determine the target heat consumption increment according to the initial heat consumption increment and the heat inhibiting factor.

14. The heat consumption estimation apparatus according to claim 8, wherein the processor-executable instructions, when executed by the one or more processors, further cause the heat consumption estimation apparatus to:

determine, after the target user finishes the motion, current basal metabolism information of the target user according to a heat consumption of the target user during this motion, and display the current basal metabolism information, wherein the current basal metabolism information is greater than basal metabolism information of the target user before this motion.

15. A non-transitory computer-readable storage medium, storing a computer program instruction, wherein the computer program instruction, when executed by one or more processors of a heat consumption estimation apparatus, causes the heat consumption estimation apparatus to:

obtain a heart rate of a target user at a current moment;

determine motion state feature information of the target user at the current moment, wherein the motion state feature information is configured to represent whether the target user is in a motion steady-state stage or a motion recovery stage at the current moment; and determine, according to the motion state feature information and the heart rate at the current moment, total heat consumption information of the target user in a motion process, wherein the motion process comprises a process from a motion starting moment to the current moment;

wherein the computer program instruction, when executed by one or more processors of a heat consumption estimation apparatus, further causes the heat consumption estimation apparatus to:

take, for each moment in a time window corresponding to the current moment, the moment as a heart rate decline moment in response to determining that a heart rate of the target user at the moment is lower than a heart rate of the target user at a previous moment of the moment, wherein the time window comprises a time period from a specified moment to the current moment, and the specified moment is earlier than the current moment; and determine the motion state feature information of the target user at the current moment according to a quantity of the heart rate decline moments;

wherein the computer program instruction, when executed by one or more processors of a heat consumption estimation apparatus, further causes the heat consumption estimation apparatus to:

determine an initial heat consumption increment of the target user within a current time period according to the heart rate at the current moment, wherein the current time period is a time period from a previous moment of the current moment to the current moment;

determine a target heat consumption increment of the target user within the current time period according to the motion state feature information and the initial heat consumption increment; and determine the total heat consumption information according to the target heat consumption increment.

* * * * *